United States Patent [19]

Hauffe

[11] Patent Number: 4,597,806

[45] Date of Patent: Jul. 1, 1986

[54] PROCESS FOR MAINTAINING THE ZINC CONTENT IN ZINC PHOSPHATE BATHS

[75] Inventor: Dieter Hauffe, Frankfurt am Main, Fed. Rep. of Germany

[73] Assignee: Parker Chemical Company, Madison Heights, Mich.

[21] Appl. No.: 751,102

[22] Filed: Jul. 2, 1985

[30] Foreign Application Priority Data

Jul. 27, 1984 [DE] Fed. Rep. of Germany ....... 3427729

[51] Int. Cl.$^4$ ................................................. C23F 7/08
[52] U.S. Cl. ................................................. 148/6.15 Z
[58] Field of Search ................................... 148/6.15 Z

[56] References Cited

U.S. PATENT DOCUMENTS 3,674,672 7/1972 Whitesell ..................... 148/6.15 Z
4,182,638 1/1980 Cooke ........................... 148/6.15 Z

*Primary Examiner*—Sam Silverberg
*Attorney, Agent, or Firm*—Arthur E. Kluegel

[57] ABSTRACT

In a process for maintaining a given zinc content in nickel-containing zinc phosphate baths, (a) nickel is precipitated in a bath sample by addition of dimethylglyoxime, a soluble copper complex compound is added and the liquid is then titrated against a copper-sensitive electrode, for determining the zinc content, with a volumetric solution containing a complexing agent for zinc and copper;

(b) the automatic metering of zinc-containing supplementary concentrate is then regulated on the basis of the deviation, ascertained in this way, from the given zinc content (prescribed value).

6 Claims, 2 Drawing Figures

PROCESS FOR MAINTAINING THE ZINC CONTENT IN ZINC PHOSPHATE BATHS

BACKGROUND OF THE INVENTION

The invention relates to a process for maintaining a given zinc content in nickel-containing zinc phosphate baths and to the application of this process to phosphatizing baths having a low zinc content.

During the practical operation of zinc phosphate baths for the chemical surface treatment of metals, bath components are consumed by formation of coatings, sludge precipitation and mechanical bath losses. These losses are compensated by addition of supplementary phosphate concentrate of appropriate composition to the phosphatizing bath. For ascertaining the consumption of chemicals and the supplementary quantity required, the current bath concentration is determined and compared with the prescribed concentration.

A customary method consists in expressing the bath concentration by the consumption of ml of N/10 NaOH for the titration of a 10-ml bath sample against phenolphthalein as indicator, ("total acid number"). A further parameter is the electric conductivity which, similar to the total acid number, also permits only an overall statement about the total concentration.

Since the introduction of the "low zinc" phosphatizing processes (German Offenlegungsschrift No. 2,232,067, German Offenlegungsschrift No. 3,101,866), the determination of the zinc content and its maintenance within narrow limits has gained special importance. For this purpose, automatic titration apparatus is employed to ascertain the cation content of the bath with the aid of complexometry, the end point being indicated colorimetrically, and the measured value thus obtained is used for adjusting the bath concentration. Since most low zinc phosphatizing baths contain, apart from zinc, also nickel, this analytical method supplies a measured value which is inaccurate due to the nickel concentration.

It is an object of the invention to provide a process for maintaining the zinc concentration in nickel-containing zinc phosphate baths which does not have the disadvantages of the known processes, works accurately and does not involve any significant expenditure for control equipment.

SUMMARY OF THE INVENTION

The object is achieved by designing the process in accordance with the invention such that
(a) nickel is precipitated in a bath sample by addition of dimethylglyoxime, a soluble copper complex compound is added and the liquid is then titrated against a copper-sensitive electrode, for determining the zinc content, with a volumetric solution, containing a complexing agent for zinc and copper and
(b) the automatic metering of zinc-containing supplementary concentrate is regulated on the basis of the deviation, ascertained in this way, from the given zinc content (prescribed value).

DETAILED DESCRIPTION OF THE INVENTION

Figure 1:
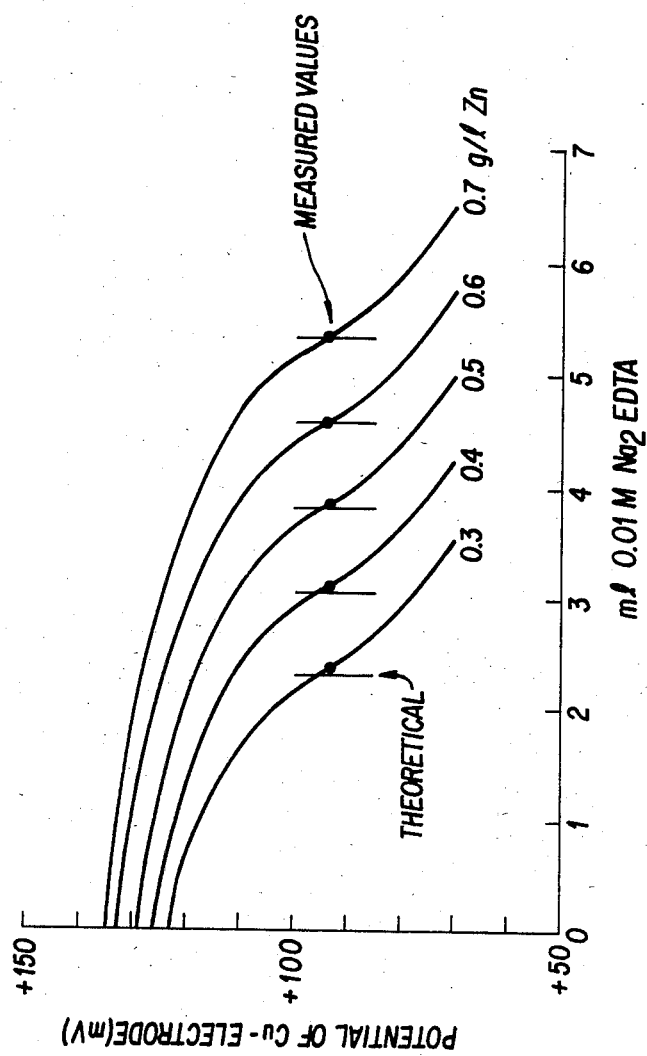
FIG. 1 is an illustration of the correlation between the potential of a copper sensitive electrode and the content of titrant based on the data obtained in accordance with Example 1.

The precipitation of nickel and the titration are carried out preferably in slightly acid range, for example at a pH value of about 5. The quantity of dimethylglyoxime, added to the sample, is preferably about 4 mol per 1 mol of Ni, that is to say, about 7 to 8 parts by weight of dimethylglyoxime per 1 part by weight of Ni. The reaction time and reaction temperature in the bath sample are not very important.

The soluble copper complex compound to be employed within the scope of the process according to the invention has to liberate, in the presence of zinc, a small quantity of $Cu^{++}$ ions in the bath sample.

A preferred embodiment of the invention provides for a complex compound of copper/ethylenediaminetetraacetic acid, at a molar ratio of 1:1, to be added to a bath sample. The quantity of copper introduced into the sample as a complex compound, expressed as a molarity, is preferably higher than the molarity of the zinc content.

A further advantageous embodiment of the invention consists in adding to a bath sample the copper complex compound in a quantity corresponding to 5 to 15 times the molar ratio (relative to Cu:Zn).

The dimethylglyoxime and the soluble copper complex compound can be added in two steps, but, alternatively, in the form of a single solution.

It is advisable for determining the zinc content, to use a volumetric solution for the titration which contains the same complexing agent which is also a component of the previously added copper complex compound. This avoids, in particular, the occurrence of possibly unforeseeable exchange reactions, which would falsify the result, between the previously added complex compound and that formed during the titration.

A further development of the invention consists therefore in carrying out the titration for determining the zinc content with a volumetric solution containing a complexing agent which is also a component of the previously added copper complex compound, or in carrying out the titration with a volumetric solution containing the disodium salt of ethylenediaminetetraacetic acid.

The molarity of the volumetric solution depends essentially on the zinc concentration of the phosphatizing bath.

A copper-sensitive electrode is immersed in the bath sample to be titrated, its potential being measured against a reference electrode, for example a calomel electrode. Copper-sensitive electrodes contain a membrane prepared, for example, from copper sulfide and silver sulfide and show a potential which depends upon the concentration of $Cu^{++}$ ions in the bath sample. The end-point of the titration coincides with the point of inflection of the potential indicated by the copper electrode. The physical explanation for this point of inflection is that the appearance of free complexing agent in the finished titrated sample is accompanied by a marked decrease in the $Cu^{++}$ ion concentration.

The zinc content ascertained by this method is used as a standard for the automatic metering of supplementary phosphate concentrate to the phosphatizing bath.

In addition to the determination of the zinc content, the total acid number may also be determined automatically. By means of these two measured values, it is possible to run a phosphatizing bath very satisfactorily at constant zinc and total acid contents, by using two supplementary concentrates, one having a higher weight ration of Zn to $P_2O_5$ (for example 0.03), the other having a lower weight ratio of Zn to $P_2O_5$ (for example 0.03). The supplementing procedure is then as set out in Table 1.

TABLE 1

| | Standard | Supplemented With Phosphate Concentrate Having | |
|---|---|---|---|
| Zn content | total acid number | high Zn to $P_2O_5$ | low Zn to $P_2O_5$ |
| too low | within the prescribed range | yes | no |
| too low | too low | no | yes |

Other bath components, for example $NaNO_2$, are supplemented automatically by known methods.

The phosphatizing baths to which the process according to the invention can be applied may contain zinc, nickel and phosphate in wide quantitative ranges and have, for example, the following concentrations:
0.2 to 2.5 g/liter of Zn,
0.2 to 2.5 g/liter of Ni
5 to 20 g/liter of $P_2O_5$ Because of its high accuracy, the process according to the invention is of special advantage for baths containing 0.2 to 1.5, preferably to 1.0 g/liter of Zn and 0.2 to 1.5 g/liter of Ni. In that case, a 0.01 M volumetric solution, particularly of the disodium salt of ethylene diamine tetracetic acid, will be appropriately used. 1 ml of this volumetric solution then corresponds to 0.65 mg of Zn.

Apart from the components mentioned, additives customary in phosphatizing technology for acceleration, oxidation, activation and coat modification may also be present.

The process according to the invention is being explained by way of example and in detail by means of the following examples.

EXAMPLE 1

For ascertaining the influence of the zinc concentration, phosphatizing bath samples containing 0.5 g/liter of Ni, 15 g/liter of $P_2O_5$ and having Zn contents of 0.3, 0.4, 0.5, 0.6 and 0.7 g/liter were prepared. The ratio of free $P_2O_5$ to total $P_2O_5$ was adjusted to 0.08.

Furthermore, a reagent A was made up from
0.017 mol/liter of diemthylglyoxime
0.085 mol/liter of Cu as a 1:1 complex with ethylenediaminetetraacetic acid
0.34 mol/liter of sodium acetate and
0.085 mol/liter of acetic acid in a 2:1 water/ethanol mixture.

The pH value of this reagent was about 5.1.

5 ml of phosphate bath sample were treated with about 10 ml of reagent A and diluted to 100 ml with distilled water. After a reaction time of 4 minutes, the sample was titrated at room temperature with 0.01 M disodium salt of ethylenediaminetetraacetic acid ($Na_2EDTA$) against a copper-sensitive electrode. The course of the potential is shown in FIG. 1. The consumption of 0.01 M volumetric solution is plotted on the abscissa, the potential of the Cu electrode in mV on the ordinate.

It is seen that the points of inflection found in practice and indicated by . are in good agreement with the theoretical consumption values for the volumetric solution, indicated by a vertical line.

EXAMPLE 2

For ascertaining the influence of the nickel concentration, phosphatizing bath samples containing 0.5 g/liter of Zn, 15 g/liter of $P_2O_5$ and having Ni contents of 0.3, 0.5 and 0.7 g/liter were prepared. The ratio of free $P_2O_5$ to total $P_2O_5$ was adjusted to 0.08.

Figure 2:
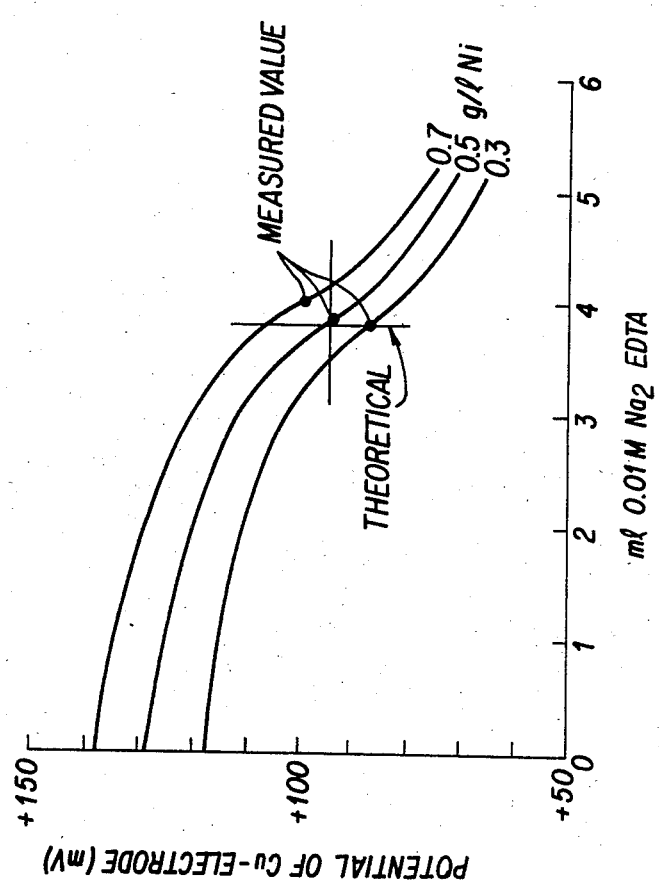
FIG. 2 is an illustration of the parameters for the same data obtained in accordance with Example 2.

As in Example 1, 5 ml of bath sample were treated with ca. 10 ml of reagent A and diluted to 100 ml with distilled water. The titration results are shown in FIG. 2. Here again, the consumption values of volumetric solution to be expected theoretically and those actually found are very close together and virtually independent of the nickel concentration.

What is claimed is:

1. A process for maintaining a given zinc content in nickel-containing zinc phosphate baths, comprising taking a sample from said bath, adding dimethylglyoxime to said sample to precipitate nickel, adding a copper complex compound to said sample, determining the zinc content by titrating the sample against a copper sensitive electrode with a volumetric solution containing a complexing agent for zinc and copper and automatically metering a zinc-containing supplementary concentrate to said bath based on the deviation from the determined zinc content and said given zinc content.

2. A process as claimed in claim 1, wherein the complex compound is copper/ethylenediaminetetraacetic acid, and is added at a molar ratio of 1:1.

3. A process as claimed in claim 1, wherein the copper complex compound is added to a bath sample in a quantity corresponding to 5 to 15 times the molar ratio (relative to Cu:Zn).

4. A process as claimed in claim 1 wherein, the complexing agent is a component of the copper complex compound.

5. A process as claimed in claim 4, wherein the titration is carried out with a volumetric solution containing the disodium salt of ethylenediaminetetraacetic acid.

6. A process as claimed in claim 1 for maintaining the given zinc content in phosphatizing baths having a zinc content of 0.2 to 1.5, g/liter of Zn.

* * * * *

UNITED STATES PATENT AND TRADEMARK OFFICE
CERTIFICATE OF CORRECTION

PATENT NO. : 4,597,806
DATED : July 1, 1986
INVENTOR(S) : Dieter Hauffe

It is certified that error appears in the above–identified patent and that said Letters Patent are hereby corrected as shown below:

| | |
|---|---|
| At column 3, line 5 | the word --ration-- should be "ratio" |
| At column 3, line 5 | the number --0.03-- should be "0.30" |
| At column 4, line 35 | the word --comples-- should be "complex" |
| At column 4, line 57 | the comma should be deleted |

Signed and Sealed this

Eighteenth Day of November, 1986

*Attest:*

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,597,806

DATED : July 1, 1986

INVENTOR(S) : Dieter Hauffe

It is certified that error appears in the above-identified patent and that said Letters Patent is hereby corrected as shown below:

On the title page assignee should read

-- (73) Assignee: Metallgesellschaft, A.G.,
              Frankfurt, West Germany --.

Signed and Sealed this

Twentieth Day of January, 1987

Attest:

DONALD J. QUIGG

Attesting Officer      Commissioner of Patents and Trademarks